United States Patent [19]

Howard et al.

[11] Patent Number: 4,938,956
[45] Date of Patent: Jul. 3, 1990

[54] SYNERGISTIC IMMUNOSTIMULATING COMPOSITION AND METHOD

[75] Inventors: David K. Howard, Arlington Heights; Ellen R. Clough, Elmhurst; Anthony F. Abruzzini, Palatine, all of Ill.; Paula Myers-Keith, Terre Haute, Ind.

[73] Assignee: International Minerals & Chemical Corp., Northbrook, Ill.

[21] Appl. No.: 32,614

[22] Filed: Apr. 1, 1987

[51] Int. Cl.$^5$ .................. A61K 37/02; A61K 39/00
[52] U.S. Cl. .................. 424/85.2; 424/88; 424/89; 424/90; 424/91; 424/92; 424/85.1; 514/2; 514/21; 514/885; 435/810
[58] Field of Search .................. 514/8, 21.2, 885; 424/85.1, 85.2, 88-92; 435/810

[56] References Cited

U.S. PATENT DOCUMENTS

| | | | |
|---|---|---|---|
| 4,311,640 | 1/1982 | Kuroda et al. | 424/85.8 |
| 4,322,341 | 3/1982 | Kitaura et al. | 424/85.8 |
| 4,349,466 | 9/1982 | Kitaura et al. | 424/85.8 |
| 4,401,756 | 8/1983 | Gillis | 435/68 |
| 4,508,833 | 4/1985 | Sonnenborn et al. | 436/543 |
| 4,518,584 | 5/1985 | Mark et al. | 424/85.1 |
| 4,604,377 | 8/1986 | Fernandes et al. | 530/351 |
| 4,606,377 | 8/1986 | Fernandes et al. | 514/8 |
| 4,780,313 | 10/1988 | Koichiro et al. | 514/8 |
| 4,789,658 | 12/1988 | Yoshimato et al. | 530/351 |

FOREIGN PATENT DOCUMENTS

| | | |
|---|---|---|
| 0158198 | 10/1985 | European Pat. Off. |
| 0158487 | 10/1985 | European Pat. Off. |
| 0095220 | 6/1984 | Japan. |
| 8504328 | 10/1985 | PCT Int'l Appl. |

OTHER PUBLICATIONS

Inamura et al., *CA* 103, 1985, #189298n.
Talmadge et al., *CA* 105, 1986, #202863f.
Kusumi, *CA* 108, 1988, #106128m.
Mine et al., CA, vol. 105, 1986, #218509f.
Mannel et al., *I Immunol* 134, 1985, pp. 3108–3110.
Souvannanong et al., *Biochem Biophys Res Comm.* 125, 1984, pp. 431–438.
Old, *Nature* 236, 1987, pp. 330–331.
Nunbey et al., CA, vol. 107, 1987, #196922x.
Henney, Chemtech, 308 (May 1987), 51:337 (1980) Reviews the Properties and Function of IL-2.
Inamura et al., Agric. Biol. Chem., 48(9):2393–2394 (1984) Reviews the Properties of FK-565.
Mine et al., J. Antibiotics, 35:1045(1983) Discloses the Use of FK-156 and FK-565 for the Enhancement of Host Resistance to Microbial Infection in Mice.
Watanabe et al., J. Antibiotics 35:1781(1985) Discloses Using FK-156 and FK-565 for the Activation of Mouse Macrophages.
Mine et al., J. Antibiotics, 35(8):1059(1983) Discloses Using FK-156 and FK-565 for the Enhancement of Host Defense Mechanisms Against Infection.
Izumi et al., J. Antibiotics, 36(5):566(1983) Discloses the Anti-Tumor Effects of FK-156 and its Synthetic Derivatives, Including FK-565.

*Primary Examiner*—Garnette Draper
*Attorney, Agent, or Firm*—Wendell R. Guffey; Thomas L. Farquer

[57] ABSTRACT

The known immunostimulants FK-565 and IL-2 are administered to animals in conjunction to synergistically stimulate the immune system.

25 Claims, 1 Drawing Sheet

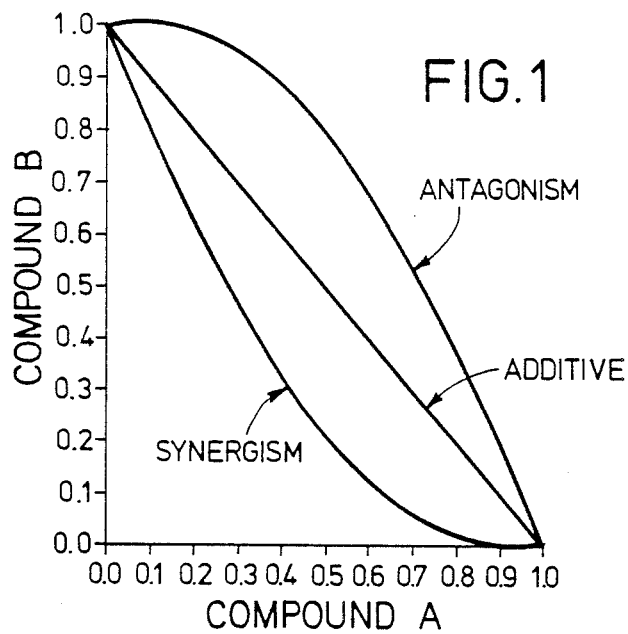
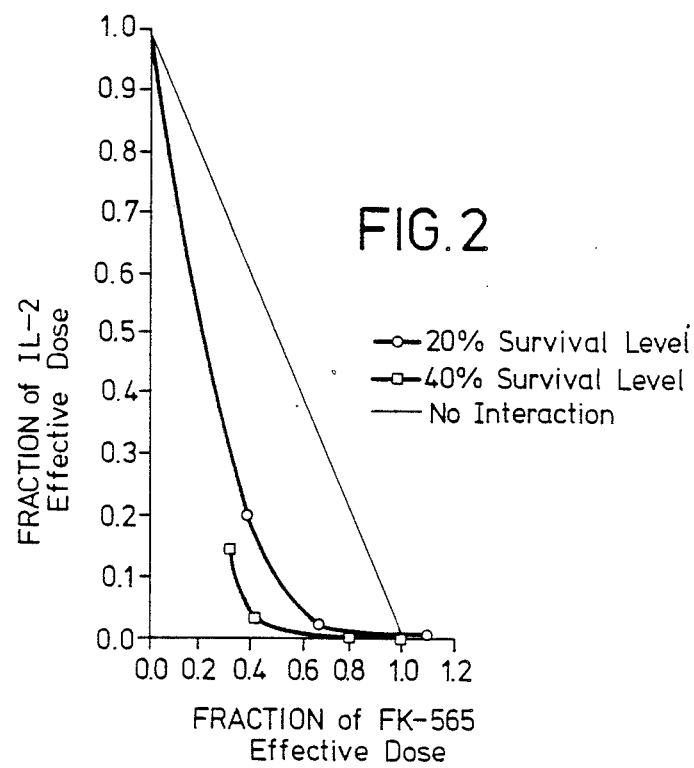

SYNERGISTIC IMMUNOSTIMULATING COMPOSITION AND METHOD

This invention relates generally to immunostimulating compositions and methods and particularly to a synergistic immunostimulating composition and method using the known immunostimulants Interleukin-2 and FK-565.

BACKGROUND OF THE INVENTION

Interleukin-2 (IL-2) is a lymphokine produced by T cells. IL-2 has a broad spectrum of growth and differentiation-promoting properties. Interleukin-2 enables T cells to grow for extended periods in vitro, enhances the immune response in animals against bacterial, parasitic, fungal, protozoan, and viral antigens, and promotes the differentiation and proliferation of killer cells. Administration of IL-2 in vivo enhances allogeneic responses and allows induction of cytotoxic and helper T cells in nude mice and chemically immunosuppressed animals. See, *Journal of Immunology*, 131:806 (1983); *Journal of Immunology*, 123:2928 (1979), *Journal of Immunology*, 130:222 (1983); and *Immunological Review*, 51:337 (1980).

Interleukin-2 was initially made by cultivating human peripheral blood lymphocytes or other interleukin-2 producing cell lines as disclosed in U.S. Pat. No. 4,401,756. However, because of difficulties in obtaining useful amounts, recombinant DNA techniques were developed to provide alternative methods for producing useful quantities of interleukin-2. Taniguchi et al., *Nature* 302:305–310 (1983) and Devos, *Nucleic Acids Research* 11:4307–4323 (1983) have reported cloning the human IL-2 gene and expressing it in microorganisms.

Subsequently, interleukin-2 analogs and derivatives having substituted, deleted, and added sequences were developed. These analogs possessed interleukin-2 activity and provided other advantages such as easier purification, easier administration, and the like. For example, Belgian Patent No. 898,016, granted Nov. 14, 1983 described muteins of IL-2 in which the cysteine normally occurring at position 125 of the wild-type or native molecule has been deleted or replaced with a neutral amino acid, such as serine. These muteins possess IL-2 biological activity. The Belgian patent states that the recombinant muteins may be formulated and administered as with native IL-2 by combining them with aqueous vehicles and injecting them intravenously, subcutaneously, or the like. U.S. Pat. No. 4,518,584 to Mark, incorporated herein by reference, discloses human recombinant IL-2 muteins having deleted or replaced cysteine residues. U.S. Pat. No. 4,508,833 to Sonneborn et al, incorporated herein by reference, reviews the methods for purifying IL-2 and discloses a purification method using dimatrix chromatography. The properties and function of IL-2 are reviewed in Smith, *Immunological Reviews*, 51:337 (1980).

FK-565 is a macrophage activator which is reported to increase host resistance to infection, induce interleukin-1 production in macrophages, and enhance phagocytic and killing activiries of macrophages. *Agric. Biol. Chem.*, 48(9):2393–2394 (1984). FK-565 is a synthetic derivative of a natural peptide FK-156 isolated from the culture filtrate of strains of *Streptomyces olivaceogriseus sp nov.* and *Streptomyces violaceus.* The isolation, purification, and structure of FK-156 has been thoroughly reviewed in the literature: *J. Antibiotics*, 35:1280–85 (1982) (Taxonomy of the Producing Strains); *J. Antibiotics*, 35:1286–92 (1982) (Fermentation, Extraction and Chemical and Biological Characterization); *J. Antibiotics*, 35:1293–99 (1982) (Structure Elucidation); and *J. Antibiotics*, 35:1300–11 (1982) (Synthesis of FK-156 and Its Geometric Isomer). U.S. Pat. No. 4,311,640 to Kuroda et al, incorporated herein by reference, discloses methods for preparing FK-156 and some of its derivatives. U.S. Pat. No. 4,322,341 to Kitaura et al, incorporated herein by reference, discloses methods for producing FK-565. U.S. Pat. No. 4,349,466 to Kitaura et al, incorporated herein by reference, discloses methods for producing several immunostimulating peptides related to FK-565.

FK-156 has the structure:

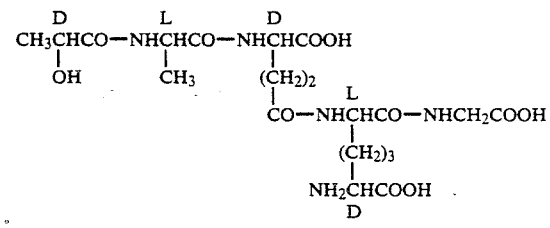

FK-565 has the structure:

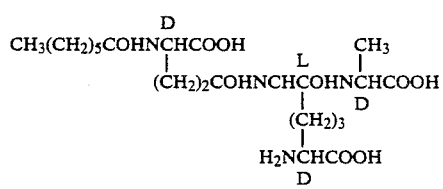

IL-2 and FK-565 are immunostimulants known to separately increase the immune system's response to invading antigens by stimulating a component of the immune system; IL-2 stimulates T cells, B cells, and macrophages and FK-565 stimulates macrophages and natural killer cells. However, the immune system's response to these and other immunostimulating agents is not always sufficient to protect the animal from disease, infections, antigens, trauma, and the like. There is, consequently, a continuing search in the art for new and better methods for stimulating the immune system. A method is, therefore, needed which can stimulate the immune system more effectively than previous immunostimulating methods and further increase the beneficial effect of immunostimulants on the immune system.

SUMMARY OF THE INVENTION

It is, therefore, an object of the present invention to provide a method and composition for stimulating the immune system.

It is another object of the present invention to provide a method and composition for synergistically stimulating the immune system.

It is another object of the present invention to provide a method for enhancing the response to an immunogen.

It is another object of the present invention to provide a method for enhancing the efficacy of a vaccine administered to an animal.

It is another object of the present invention to provide a composition which will function as an adjuvant.

It is a further object of the present invention to provide an article of manufacture containing the compounds of the present invention.

These and other objects are achieved by administering FK-565 and IL-2 in conjunction to stimulate the animal's immune system. FK-565 and IL-2 administered in conjunction produce both additive and synergistic levels of survival in animals challenged with lethal levels of encephalomyocarditis virus or pseudorabies virus. In addition, FK-565 and IL-2 administered in conjunction cause proliferation in vitro of murine lymphocytes where the proliferation is synergistic, i.e. greater than the sum of those seen with either compound alone. The compounds can be placed in containers or dosage forms appropriately selected depending upon the desired administration route.

DESCRIPTION OF THE DRAWINGS

FIG. 1 shows hypothetical response curves after isobologram analysis.

FIG. 2 shows isobologram analysis of interactions of FK-565 and IL-2 in Pseudorabies Virus infected mice.

DETAILED DESCRIPTION OF THE INVENTION

Some terms used herein are defined as follows:

"IL-2" is defined to include the natural and recombinant interleukin-2 molecules and their muteins, analogs, and derivatives having deleted, inserted, or otherwise modified sequences which possess native interleukin-2 activity.

A "unit" of IL-2 as used herein is defined as the quantity of material sufficient to stimulate half-maximal incorporation of tritiated thymidine by IL-2-sensitive cell lines (such as CTLL-2 available from the American Type Culture Collection) in a standardized assay; See, Gillis et al., *Journal of Immunology*, 120:2027 (1978).

The term "adjuvant" means any substance which when administered in conjunction with an antigen heightens, or affects the qualities of, the immune response to that antigen. Adjuvants are commonly administered with the object of increasing the immunogenicity of an antigen in order to stimulate a higher rate of antibody formation or a more vigorous response in cell mediated immunity with respect to that antigen.

The term "vaccine" means any immunogenic preparation dosage form administered with the result of stimulating the recipients specific immune defense mechanisms in respect of given pathogenic or toxic agents. Generally vaccine dosages contain (a) inactivated antigens such as those used to vaccinate for typhoid and cholera, (b) live attenuated antigens such as those used to vaccinate for yellow fever and tuberculosis, (c) antigenic extracts of specific antigens, (d) sub-unit vaccines derived by recombinant DNA technology, and (e) toxoids. Vaccines known in the art are typically formulations of antigens that stimulate the animal immune system, typically formulations of attenuated viruses, inactivated viruses, killed bacteria, subunits of viruses or bacteria, "engineered" live virus or bacteria, or small doses of live bacteria, viruses, or other pathogens.

The term "in conjunction" means that FK-565 and IL-2 are administered to the animal (1) separately at the same or different frequency using the same or different administration routes or (2) together in a pharmaceutically acceptable composition.

The term "parenterally" means administration by intravenous, subcutaneous, intramuscular, or intraperitoneal injection, or by subcutaneous implant.

The term "synergism" means a cooperative effect between individual compounds such that the total effect is greater than the sum of the effects of the compounds taken independently.

The method of the present invention comprises administering FK-565 and IL-2 in conjunction to synergistically stimulate the immune system. The composition of the present invention comprises the compounds IL-2 and FK-565 or in combination with pharmaceutically acceptable carriers such as various vehicles, adjuvants, additives, and diluents. The article of manufacture of the present invention comprises a first container containing an immunostimulating amount of FK-565 in a pharmaceutically acceptable carrier suitable for parenteral or oral administration and a second container containing an immunostimulating amount of IL-2 in a pharmaceutically acceptable carrier suitable for parenteral administration. Alternatively, the article of manufacture may comprise a container containing an immunostimulating amount of IL-2, FK-565, and a pharmaceutically acceptable carrier suitable for parenteral administration.

FK-565 and IL-2 according to the present invention are administered to animals with poorly functioning immune systems typically caused by malnutrition, trauma, infection, or diseases, but preferably are administered to healthier animals to synergistically stimulate the immune system and increase resistance to infection and disease and decrease the recovery time from injury or other trauma. The compounds of the present invention can, therefore, be used therapeutically or prophylactically. Because of the synergistic interaction of the compounds, the dosages of the compounds can be decreased resulting in a lower cost for administration and decreasing any undesirable side effects associated with high dosages of the compounds.

Preferably, FK-565 and IL-2 are administered at about the same time but, if administration is difficult, the compounds are effective as immunostimulants if administered in conjunction. For example, FK-565 can be administered orally, e.g. in tablets, capsules, feed and water compositions, and IL-2 can be injected into the animal within a short time, generally within 48 hours, preferably within 24 hours, and most preferably within 1–8 hours.

FK-565 and IL-2 can be administered in a single dose or can be administered in multiple doses over a period of time, generally by injection or, for FK-565, in the animal's feed. For example, FK-565 can be administered orally as a single dose and IL-2 can be administered by daily injection over a period of several days. Similarly, FK-565 can be administered orally, preferably in the animal's feed, in multiple doses over a period of several days and IL-2 can be administered by daily injection over a period of several days. Many such administration patterns will be apparent to those skilled in the art.

The amount of IL-2 and FK-565 administered may vary depending upon the particular type of animal, the maturity of the animal, the size of the animal, the administration pattern, and whether the dose is to act therapeutically or prophylactically. Generally, FK-565 and IL-2 are administered to the animal according to the present invention in dosages from 0.001–1000 μg FK-565/kg of body weight, preferably from 0.01–10 μg FK-565/kg of body weight, and from about $10^1$–$10^8$ units IL-2/animal, preferably from about $10^2$–$10^7$ units/animal.

FK-565 and IL-2 can be administered as the compound or as a pharmaceutically acceptable salt of the compound, alone, in combination, or in combination with pharmaceutically acceptable carriers, diluents, and vehicles. The carrier can be an antibiotic, other immune stimulating agent, an inert carrier, and the like. Most preferably, FK-565 and IL-2 are mixed individually or in combination with pharmaceutically acceptable carriers to form compositions which allow for easy dosage preparation.

The FK-565 and IL-2 composition of the present invention can be administered to the animal in any acceptable manner including by injection, using an implant, and the like. Injections and implants are preferred because they permit precise control of the timing and dosage levels used for administration, with injections being most preferred. FK-565 and IL-2 compositions according to the present invention are preferably administered parenterally.

FK-565 according to the present invention can be administered to the animal in any acceptable manner including orally, by injection, using an implant, nasally, and the like. Oral administration includes administering the composition of the present invention in tablets, suspensions, implants, solutions, emulsions, capsules, powders, syrups, water compositions, feed compositions, and the like. Nasal administration includes administering the composition of the present invention in sprays, solution, and the like. Injections and implants are preferred because they permit precise control of the timing and dosage levels used for administration, with injections being most preferred. FK-565 is preferably administered parenterally.

IL-2 according to the present invention can be administered to the animal in any acceptable manner including by injection, using an implant, and the like. Injections and implants are preferred because they permit precise control of the timing and dosage levels used for administration, with injections being most preferred. IL-2 is preferably administered parenterally; oral administration is not favored because the bioactivity of IL-2 is destroyed by enzymes in the digestive tract.

FK-565, IL-2, and FK-565 and IL-2 compositions can be administered to the animals in an injectable formulation containing any IL-2 and FK-565 compatible and biocompatible carrier such as various vehicles, adjuvants, additives, and diluents to achieve a composition usable as a dosage form. FK-565 is added to the carrier in amounts sufficient to supply from about 0.001–1000 $\mu$g FK-565/kg of body weight to the animal when injected. IL-2 is added to the carrier in amounts sufficient to supply from about $10^1$–$10^8$ units to the animal when injected. Preferably, the compounds are added to a the carrier in amounts sufficient to supply from about 0.01–10 $\mu$g FK-565/kg of body weight and from about $10^2$–$10^7$ units IL-2/animal.

Aqueous vehicles such as water having no nonvolatile pyrogens, sterile water, and bacteriostatic water are also suitable to form injectable IL-2 and FK-565 formulations. In addition to these forms of water, several other aqueous vehicles can be used. These include isotonic injection compositions that can be sterilized such as phosphate buffered saline, sodium chloride, Ringer's, dextrose, dextrose and sodium chloride, gelatin and lactated Ringer's. Addition of water-miscible solvents, such as methanol, ethanol, or propylene glycol generally increases solubility and stability of the compounds in these vehicles.

Nonaqueous vehicles such as cottonseed oil, squalene, sesame oil, or peanut oil and esters such as isopropyl myristate may also be used as solvent systems for IL-2 and FK-565. Additionally various additives which enhance the stability, sterility, and isotonicity of the composition including antimicrobial preservatives, antioxidants, chelating agents, gelatin and buffers can be added. Any vehicle, diluent, or additive used would, however, have to be compatible with the compounds of the present invention.

FK-565, IL-2, and FK-565 and IL-2 compositions according to the present invention can be administered to the animal in the form of a slow-release subcutaneous implant which is inserted beneath the skin of the animal. The implant can take the form of a pellet which slowly dissolves after being implanted in the animal or a biocompatible and IL-2 and FK-565 compatible delivery module well known to those skilled in the art. Such well known dosage forms are designed such that the active ingredients are slowly released over a period of several days to several weeks. The implant is designed to deliver from about 0.001–1000 $\mu$g FK-565/kg of body weight/day, preferably from about 0.01–10 $\mu$g FK-565/kg of body weight/day, to the animal and from about $10^1$–$10^8$ units IL-2/animal/day, preferably from about $10^2$–$10^7$ units/animal/day.

FK-565 according to the present invention can be administered orally to the animal. For example, the FK-565 can be blended with ordinary feed compositions or added to drinking water in amounts sufficient to stimulate the animal's immune system. When FK-565 is to be administered in feeds, an animal feed composition may be prepared containing the usual nutritionally-balanced feed containing quantities of carbohydrates, proteins, vitamins and minerals, together with FK-565 in accordance with the present invention. Some of the usual dietary elements included in animal feed compositions are grains, such as ground grain and grain byproducts, animal protein substances, such as those found in fish meal and meat scraps, vegetable proteins, like soybean oil meal or peanut oil meal; vitamins and vitamin-containing materials, e.g., vitamin A and D mixtures, riboflavin supplements and other vitamin B complex members; and bone meal and limestone to provide minerals. A type of conventional feed material for use with cattle includes alfalfa hay and ground corncobs together with supplementary vitamins and vitamin-containing substances if desired. FK-565 according to the present invention is admixed with the feed in amounts sufficient to supply from about 0.001–1000 $\mu$g/kg body weight/day, typically 1–100 g/ton of feed, to the animal.

FK-565, IL-2, and FK-565 and IL-2 compositions according to the present invention are useful for stimulating the immune system of animals which are susceptible to or suffering from various infections and diseases such as, but not limited to pseudorabies, transmissible gastroenteritis, IBR, BVD, PI3, shipping fever, influenza, hoof and mouth disease, and the like. Additionally, FK-565 and IL-2 are useful for stimulating the immune system of animals recovering from surgery, injury, stress, infection, or other trauma. Stimulating the immune system improves the chance of survival and recovery time and increases the resistance to infections and disease.

Any animal species having an immune system can be administered FK-565, IL-2, and FK-565 and IL-2 compositions according to the present invention. Human, bovine, porcine, canine, feline, equine, avian, and ovine are preferred, with livestock and poultry such as cattle, swine, sheep, chickens, and turkeys being most preferred.

FK-565, IL-2, and FK-565 and IL-2 compositions are also useful as injectable vaccine adjuvants when used in conjunction with vaccines such as, but not limited to, those for influenza, hoof and mouth disease, hepatitis, rabies, distemper, meningitis, cholera, enteritis, diphtheria, measles, mumps, and the like. The compounds may be incorporated in the dose of the vaccine in an amount from about 0.001–100 µg FK-565, preferably from about 0.01–10 µg, and $10^1$–$10^8$ units, preferably from about $10^2$–$10^7$ units, IL-2 per dose of vaccine, preferably with a pharmaceutically-acceptable vehicle or carrier such as a fat or lipid emulsion or glycerol. The animal is vaccinated by administering the vaccine-adjuvant dose to the animal in the manner conventional for the particular vaccine.

Alternatively, the animal is vaccinated by administering the compounds in conjunction independently of the vaccine. The compounds are administered prior to, contemporaneously with, or subsequent to vaccine administration, preferably about 8–24 hours prior to administration of the vaccine. The compounds stimulate the immune system thereby improving the response to the vaccine.

Although not wishing to be bound by theory, it is believed that FK-565 and IL-2 according to the present invention stimulate macrophages and T cells in the immune system. FK-565 and IL-2 also synergistically stimulate the immune system to increase the survivability of test animals presented with lethal bacteria and virus challenge.

Advantageously, an article of manufacture comprising a first container containing an immunostimulating amount of FK-565 in a pharmaceutically acceptable carrier suitable for parenteral or oral administration and a second container containing an immunostimulating amount of IL-2 in a pharmaceutically acceptable carrier suitable for parenteral administration is provided according to the present invention. The article of manufacture contains from about 0.001–1000 µg FK-565/kg body weight in the first container and from about $10^1$–$10^8$ units IL-2 in the second container. Also, an article of manufacture comprising a container containing an immunostimulating amount of IL-2, FK-565, and a pharmaceutically acceptable carrier is provided according to the present invention. The article of manufacture contains from about 0.001–1000 µg FK-565/kg body weight and from about $10^1$–$10^8$ units IL-2.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

The Aujesky strain of pseudorabies virus (ATCC VR-135) and encephalomyocarditis virus (ATCC VR-129) were obtained from the American Type Culture Collection.

Four to six week old female CF1 mice were acclimated for 7 to 10 days before the start of each study. During this time and for the duration of all studies they were allowed food and water ad libitum.

FK-565 and IL-2 were administered in varying dosages (Table 1–4) once per day for three consecutive days, beginning three days before infecting the mice (days −3, −2, −1) with virus. On day 0, the mice received an intraperitoneal injection of either pseudorabies virus (PrV) or encephalomyocarditis virus (EMC) in 0.2 ml to 0.4 ml of Dulbecco's Modified Eagle's Medium. The dose of virus used was a dose previously determined to cause 80% lethality in untreated mice. Mortality levels were monitored daily for 10 to 14 days.

Survival data were analyzed using binomial distribution tables and by comparison of median survival times. Interactions between compounds administered as a combination treatment were analyzed by construction of isobolograms. The results are summarized in Tables 1–4. The isobolograms are shown in FIGS. 1 and 2.

Referring to Table 1, in EMC virus infected mice, treatment with combinations of FK-565 and IL-2 resulted in greater survival than seen with either compound alone. The survival levels after some combination treatments were statistically different from untreated animals whereas treatment with either compound alone showed no statistical difference.

Referring to Table 2, combination treatments also increased median survival times over those seen with either compound alone. In experiment 3, treatment of 500 µg/kg FK-565 resulted in a median survival time of 7 days. Treatment with 1000 units of IL-2 alone resulted in a median survival time of 5 days. Treatment with a combination of 500 µg/kg FK-565 and 1000 units IL-2 resulted in a median survival time of 10 days.

Referring to Table 3, combination treatments given to pseudorabies virus infected mice had an even more dramatic effect. FK-565 and IL-2 administered in conjunction resulted in better than additive (synergistic) effects on survival as well as dramatic increases in median survival times. Survival after treatment with some combinations of FK-565 and IL-2 was statistically different from treatment with either compound alone.

Referring to Table 4, combinations containing 100 or 500 µg/kg FK-565 and 100 or 1,000 units IL-2 result in a greater than two-fold increase in median survival times.

As well known in the art, isobologram analysis is widely used to analyze interactions of antibiotics. This technique was applied to the analysis of interactions between FK-565 and IL-2. A theoretical depiction of the different kinds of possible interactions between two compounds is shown in FIG. 1. The concentration of each of two compounds required to produce a desired result (50% effective dose, 80% death, etc.) is calculated for each compound alone and in the presence of varying amounts of the other compound. For FK-565 and IL-2, the concentrations were determined by regression analysis of survival curves of mice treated with various doses of either compound alone, or in combination with different doses of the other compound. Results were plotted as percentages of the effective dose in the absence of the other compound.

If the two hypothetical compounds A and B are neither stimulators nor inhibitory to the other compound, they are termed additive and the result is a straight line labeled as "additive" in FIG. 1. If compound A inhibits the action of compound B, then at any concentration of A a greater concentration (as percent of effective dose) of B is required to obtain the effect seen in the absence of A. This results in the line labeled "antagonism" in FIG. 1. Similarly, if compound A has a stimulatory effect on compound B, less of B will be required to obtain the same result in the presence of A as you find in the absence of A. This is labeled "synergism" in FIG. 1.

When this analysis is applied to combinations of FK-565 and IL-2, the results shown in FIG. 2 are obtained. These results clearly show a surprisingly synergistic interaction of FK-565 and IL-2.

EXAMPLE 2

To test the effect of administering the compounds at different times, mice were treated with FK-565 and IL-2 in conjunction for three days before infection with pseudorabies virus, for three days beginning one day before infection and for three days beginning either one or two days after infection. The results are shown in Table 5.

Referring to Table 5, treatment with FK-565 or with combinations of FK-565 and 1,000 units IL-2 still resulted in statistically significant enhancement of survival when treatment was started one day before infection. When treatment was started one day after infection, one combination still resulted in synergistic effects. When treatment was started two days after infection no statistically significant changes in survival were seen. These results indicate that FK-565 and IL-2 should preferably be used prophylactically or soon after exposure to virus to be efficacious. The highest survival levels were seen when the treatments began 3 days before infection.

EXAMPLE 3

The efficacy of treatments given beginning 7 and 3 days before infection was tested. Mice were treated with various combinations of FK-565 and IL-2 for 3 consecutive days and infected either 1 or 4 days after treatment ceased. The results are shown in Table 6.

Referring to Table 6, treatment was most effective in increasing survival when administered beginning 3 days before infection. Synergism was still evident with a number of combination treatments begun 7 days before infection but, in general, treatment was more effective if started 3 days before infection.

EXAMPLE 4

Effects of IL-2 and FK-565 on the One-way Murine Mixed Lymphocyte Response:

The mixed lymphocyte response (MLR) is indicative of the ability of T-cells to recognize non-self determinants on cells from another animal. Since rIL-2 acts primarily as a T-cell growth factor, it would be expected that this compound should modulate this response. Spleen cells were isolated from mice of two genetically different strains (with respect to major histocompatibility complex I-region antigens) and used as responders and stimulators in this assay. Cells isolated from C57BL/6 mice served as the responder population while cells isolated from Balb/c mice served as the stimulator population. Stimulator cells were pre-treated with either mitomycin-C or radiation (3300 rads) to prevent them from incorporating tritiated thymidine into DNA. Thus, any proliferation as measured by tritiated thymidine uptake would have to result from the responder cells. Since only one of the two cell populations in this assay can respond to stimulation, this is referred to as a one-way MLR. The results are shown in Table 7.

Referring to Table 7, the one-way MLR has been optimized with respect to cell culture media and time of incubation. The addition of various amounts of rIL-2 alone has little, if any, effect. However, interactive effects of rIL-2 and FK-565 leading to enhanced responsiveness were evident even under optimized culture conditions. Combinations of 10 nanogram per milliliter (ng/ml) of rIL-2 and either 0.1 or 1.0 $\mu$g/ml of FK-565 led to surprisingly synergistic responses greater than those achieved with either compound alone.

EXAMPLE 5

Effects of IL-2 and FK-565 on the Primary Immunization of Murine Spleen Cells In Vitro The primary immunization of murine spleen cell (in vitro), often referred to as the Mishell-Dutton culture system, is an excellent model for the primary antibody response to antigen (in vivo). The assay systems measure antibody-producing-cells in the spleen by enumerating plaque-forming-cells in the slide modification of the Jerne plaque assay and serum antibody titers using a hemagglutination assay. The model antigen used was the sheep erythrocyte (SRBC or ShE). Blood samples taken from individual donor sheep (Colorado Serum Company) were obtained and screened. All assays were performed with erythrocytes isolated from a single donor animal. The results are shown in Table 8.

Referring to Table 8, when added to splenocyte cultures at initiation, rIL-2 augmented the formation of plaque-forming-cells (PFCs) in a dose dependent fashion. PFCs were readily detected in treated cultures at day 3, where no APCs could be detected in control cultures. At days 4 and 5, treated cultures yielded substantially more PFCs than untreated cultures. Optimal responses in treated cultures occurred at day 4, while optimal responses in untreated cultures did not occur until day 5. Interactive effects were observed between rIL-2 and FK-565 on the PFC response of spleen cell cultures. The kinetics of the PFC response varied with dosages: increasing concentrations of FK-565 shifted the kinetics of the PFC response to 10 ng/ml of rIL-2 so that peak responses occurred on day 5, rather than on day 4. Surprisingly, the magnitudes of the peak responses in cultures given both rIL-2 and FK-565 were also increased over cultures given rIL-2 alone.

EXAMPLE 6

Spleens were removed sterily from OVA-FITC (a protein conjugate consisting of ovalbumin and fluorescein isothiocyanate) immunized mice and single cell suspensions were made in Hanks Balanced Salt Solution (HBSS). The cells were washed three times and brought to a final concentration of $2.5 \times 10^6$ cells/ml in RPMI 1640 cell culture medium containing antibiotics, L-glutamine, 2-mercaptoethanol, HEPES buffer and 10% fetal calf serum. Triplicate cultures containing 0, 2.5, 5 or 10 $\mu$g/ml OVA-FITC were initiated in 96 well tissue culture plates. Each well of the triplicate cultures also contained 0, 0.01, or 0.1 $\mu$g/ml FK-565 and 0, 0.3, or 0.6 $\mu$g/ml rIL-2. The cultures were maintained in 5% $CO_2$ in air at 37° C. for 3 days, when 1 $\mu$l [3H]-thymidine was added to each well. Twenty-four hours later the cultures were harvested using a Skatron Cell Harvester. Samples were placed in a scintillation counter and data were recorded as the number of counts/minute (CPM). The results are shown in Table 9.

Referring to Table 9, FK-565 alone stimulates a low level of in vitro cell proliferation as measured by $^3$H-thymidine incorporation over the 4 day culture period. Addition of 0.1 μg/ml FK-565 roughly triples the response over that seen for cultures containing no FK-565. When increasing concentrations of rIL-2 are added to cultures there is a surprising 8 fold increase in CPM. rIL-2 added to cultures containing FK-565, results in a synergistic interaction, with proliferation 24 times background levels. FK-565 added to cultures containing antigen does not increase proliferation of antigen stimulated cells. rIL-2 added to cultures containing 5 μg/ml OVA-FITC causes a 2.5 fold increase over background CPM. When 0.6 μg/ml rIL-2 and 0.1 μg/ml FK-565 are added, cell proliferation, as measured by thymidine incorporation increases to a level 6 times over background.

EXAMPLE 7

Bovine gut lamina proprial lymphocytes were obtained by placing pieces of bovine intestine in a flask containing calcium and magnesium free (CMF) Hanks Balanced Salt Solution (HBSS) containing 0.5 g/liter EDTA with constant stirring. The supernatant was removed every 15 minutes until the supernatant was clear. The pieces were washed and incubated at 37° C. in a shaking water bath for 90 minutes in CMF HBSS with 5% Fetal Calf Serum (FCS), 10 units/ml collagenase, and an equal weight of soybean trypsin inhibitor. Cells were washed twice in HBSS with 5% FCS and placed in culture at a concentration of $5 \times 10^6$ cell/ml.

Triplicate cultures contained 0, 0.0312, 0.0625, 0.125, 0.25, 0.5, 1 or 2 μg/ml FK-565 with or without 3.75, 15, or 30 nanogram (ng)/ml rIL-2. The cultures were maintained in 5 percent $CO_2$ in air at 37° C. for 4 days, when 1 μl $^3$H-thymidine was added to each well. Twenty-four hours later the cultures were harvested using a Skatron Cell Harvester. Samples were placed in a scintillation counter and data were recorded as the number of counts/minute (CPM). The results are shown in Table 10.

Referring to Table 10, cells did not proliferate in response to treatment with any of the concentrations of FK-565, nor did they respond to 3.75 ng/ml rIL-2 although proliferation occurs with 15 or 30 ng/ml. Stimulation with FK-565 and 3.75 ng/ml rIL-2 did not result in proliferation. However 15 ng/ml rIL-2 with 2 μg/ml FK-565 stimulated a 5 fold increase over background levels. Treatment with 30 ng/ml rIL-2 resulted in maximal proliferation even in the absence of FK-565.

TABLE 1

Percent Survival of EMC Virus Infected Mice after Treatment with Combinations of FK-565 and Recombinant IL-2

| FK-565 μg/kg | IL-2 units | Exp 1 | Exp 2 | Exp 3 | Exp 4 | Mean |
|---|---|---|---|---|---|---|
| 0 | 0 | 20 | 55 | 30 | 40 | 36 |
| 0 | 10 | 20 | — | — | 20 | 20 |
| 0 | 100 | 40 | — | 10 | 47 | 32 |
| 0 | 1000 | 50(1) | 70 | 15 | 87(2) | 56 |
| 4 | 0 | — | — | — | 93(6) | 93 |
| 4 | 10 | — | — | — | 40 | 40 |
| 4 | 100 | — | — | — | 40 | 40 |
| 4 | 1000 | — | — | — | 73(5) | 73 |
| 20 | 0 | — | 50 | 30 | 60(3) | 47 |
| 20 | 10 | — | — | — | 60(3) | 60 |
| 20 | 100 | — | 60 | 55(4) | 53(1) | 56 |
| 20 | 1000 | — | 86 (4) | 45 | 60(3) | 64 |
| 100 | 0 | 10 | 60 | 65(5) | 67(1) | 51 |
| 100 | 10 | — | — | — | 60(3) | 60 |
| 100 | 100 | — | 60 | 45 | 73(5) | 59 |
| 100 | 1000 | — | 100 (6) | 75(6) | 67(1) | 81 |
| 500 | 0 | — | 70 | 30 | 73(5) | 62 |
| 500 | 10 | — | — | — | 67(1) | 67 |
| 500 | 100 | — | 50 (1) | 25 | 73(5) | 49 |
| 500 | 1000 | — | 70 | 70(5) | 93(6) | 78 |

Figures in parentheses represent statistical significance as determined from binomial and Poisson distribution tables as follows:
1. $P < 0.03$;
2. $P < 0.003$;
3. $P < 0.09$;
4. $P < 0.02$;
5. $P < 0.0001$;
6. No probability of randomness

TABLE 2

Median Survival Times Days of EMC Infected Mice after Treatment with Combinations of FK-565 and Recombinant IL-2

| FK-565 μg/kg | IL-2 units | Exp 1 | Exp 2 | Exp 3 | Exp 4 | Average |
|---|---|---|---|---|---|---|
| 0 | 0 | 5 | 10 | 5 | 7 | 6.8 |
| 0 | 10 | 4 | — | — | 6 | 5 |
| 0 | 100 | 4.5 | — | 5 | 6 | 5 |
| 0 | 1000 | 4 | 10 | 5 | 10 | 7.3 |
| 4 | 0 | — | — | — | 10 | 10 |
| 4 | 10 | — | — | — | 8 | 8 |
| 4 | 100 | — | — | — | 6 | 6 |
| 4 | 1000 | — | — | — | 10 | 10 |
| 20 | 0 | — | 9.5 | 5 | 10 | 8.2 |
| 20 | 10 | — | — | — | 10 | 10 |
| 20 | 100 | — | 10 | 10 | 10 | 10 |
| 20 | 1000 | — | 10 | 6.5 | 10 | 8.8 |
| 100 | 0 | 5.5 | 10 | 10 | 10 | 8.8 |
| 100 | 10 | — | 0 | 0 | 10 | 10 |
| 100 | 100 | — | 10 | 9 | 10 | 9.7 |
| 100 | 1000 | — | 10 | 10 | 10 | 10 |
| 500 | 0 | — | 9.5 | 7 | 10 | 9 |
| 500 | 10 | — | — | — | 10 | 10 |
| 500 | 100 | — | 9.5 | 6 | 10 | 8.5 |
| 500 | 1000 | — | 10 | 10 | 10 | 10 |

TABLE 3

Percent Survival of Pseudorabies Virus Infected Mice After Treatment with Combinations of FK-565 and Recombinant IL-2

| FK-565 μg/kg | IL-2 units | Exp 1 | Exp 2 | Exp 3 | Exp 4 | Exp 5 | Mean |
|---|---|---|---|---|---|---|---|
| 0 | 0 | 0 | 0 | 0 | 10 | 25 | 7 |
| 0 | 10 | 0 | 13 | 7 | — | 10 | 7.5 |
| 0 | 100 | 0 | 7 | 0 | — | 25 | 8 |
| 0 | 1000 | 7 | 0 | 0 | 5 | 35 | 9.4 |
| 0 | 5000 | — | — | 20 | 0 | 0 | 20 |
| 4 | 0 | 0 | 7 | — | — | — | 3.5 |
| 4 | 10 | 33 (1) | 0 | — | — | — | 16.5 |
| 4 | 100 | 0 | 20 (2) | — | — | — | 10 |
| 4 | 1000 | 20 (2) | 0 | — | — | — | 10 |
| 20 | 0 | 20 (2) | 13 | 13 | — | 55 (3) | 25 |

TABLE 3-continued

Percent Survival of Pseudorabies Virus Infected Mice After Treatment with Combinations of FK-565 and Recombinant IL-2

| FK-565 μg/kg | IL-2 units | Experiment 1 | 2 | 3 | 4 | 5 | Mean |
|---|---|---|---|---|---|---|---|
| 20  | 10   | 20 (2) | 13     | 7      | —      | —       | 13.3 |
| 20  | 100  | 20 (2) | 27 (3) | 33 (4) | —      | 85 (5)  | 41 |
| 20  | 1000 | 20 (2) | 40 (5) | 27 (3) | —      | 90 (5)  | 44 |
| 20  | 5000 | —      | —      | 40 (5) | —      | —       | 40 |
| 100 | 0    | 33 (4) | 27 (3) | 27 (3) | 35 (4) | 80 (5)  | 40 |
| 100 | 10   | 40 (6) | 20 (2) | 13     | —      | 85 (5)  | 40 |
| 100 | 100  | 33 (4) | 33 (4) | 40 (5) | —      | 85 (5)  | 35 |
| 100 | 1000 | 67 (5) | 73 (5) | 33 (4) | 60 (5) | 100 (5) | 68 |
| 100 | 5000 | —      | —      | 53 (5) | —      | —       | 53 |
| 500 | 0    | 0      | 40 (5) | 33 (4) | 65 (5) | 80 (5)  | 44 |
| 500 | 10   | 27 (3) | 20 (2) | 47 (5) | —      | —       | 31 |
| 500 | 100  | 40 (5) | 60 (5) | 53 (5) | —      | 80 (5)  | 58 |
| 500 | 1000 | 60 (5) | 60 (5) | 73 (5) | 70 (5) | 100 (5) | 73 |
| 500 | 5000 | —      | —      | 73 (5) | —      | —       | 73 |

Numbers in parentheses represent statistical significance as determined from binomial and Poisson distribution tables:
1. $P < 0.0004$;
2. $P < 0.03$;
3. $P < 0.004$;
4. $P < 0.0004$;
5. No probability of randomness;
6. $P < 0.0001$.

TABLE 4

Median Survival Times of Mice Infected with Pseudorabies Virus after Treatment with Combinations of FK-565 and Recombinant IL-2

| FK-565 μg/kg | IL-2 units | Experiment 1 | 2 | 3 | 4 | 5 | Average |
|---|---|---|---|---|---|---|---|
| 0   | 0    | 3  | 3  | 3  | 3  | 4  | 3.2 |
| 0   | 10   | 3  | 3  | 3  | —  | 4  | 3.3 |
| 0   | 100  | 3  | 3  | 3  | —  | 4  | 3.3 |
| 0   | 1000 | 3  | 3  | 3  | 4.5| 5  | 3.7 |
| 0   | 5000 | —  | —  | 3  | —  | —  | 3 |
| 4   | 0    | 3  | 4  | —  | —  | —  | 3.5 |
| 4   | 10   | 4  | 4  | —  | —  | —  | 4 |
| 4   | 100  | 4  | 3  | —  | —  | —  | 3.5 |
| 4   | 1000 | 4  | 4  | —  | —  | —  | 4 |
| 20  | 0    | 4  | 5  | 3  | —  | 9.5| 5.4 |
| 20  | 10   | 4  | 5  | 3  | —  | —  | 4 |
| 20  | 100  | 4  | 4  | 4  | —  | 10 | 5.5 |
| 20  | 1000 | 5  | 5  | 3  | —  | 10 | 5.8 |
| 20  | 5000 | —  | —  | 7  | —  | —  | 7 |
| 100 | 0    | 4  | 4  | 3  | 5  | 10 | 5.4 |
| 100 | 10   | 6  | 4  | 3  | —  | 10 | 5.8 |
| 100 | 100  | 6  | 4  | 4  | —  | 10 | 6 |
| 100 | 1000 | 6  | 10 | 3  | 10 | 10 | 7.8 |
| 100 | 5000 | —  | —  | 10 | —  | —  | 10 |
| 500 | 0    | 4  | 5  | 4  | 10 | 10 | 6.6 |
| 500 | 10   | 4  | 3  | 5  | —  | —  | 4 |
| 500 | 100  | 6  | 10 | 10 | —  | 10 | 9 |
| 500 | 1000 | 10 | 10 | 10 | 10 | 10 | 10 |
| 500 | 5000 | —  | —  | 10 | —  | —  | 10 |

Median survival times are expressed in days

TABLE 5

Percent Survival of Pseudorabies Virus Infected Mice Treated with Combinations of FK-565 and Recombinant IL-2 at Different Times Before and After Infection

| Treatment FK-565 μg/kg | IL-2 units | Day of Initiation of Treatment/Survival −3 | −1 | +1 | +2 |
|---|---|---|---|---|---|
| 0   | 0    | 30     | 30     | 30     | 30 |
| 100 | 0    | 90(1)  | 75(1)  | 30     | N.D. |
| 500 | 0    | 95(1)  | 75(1)  | 55(2)  | 40 |
| 0   | 1000 | 50(1)  | 30     | 15     | 10 |
| 100 | 1000 | 95(1)  | 70(1)  | 55(2)  | N.D. |
| 500 | 1000 | 90(1)  | 70(1)  | 20     | 25 |

Numbers in parentheses refer to statistical significance determined from binomial and Poisson distribution tables:
1. No probability of randomness;
2. $P < 0.02$.
N.D. = Not determined.

TABLE 6

Survival of Pseudorabies Virus Infected Mice after Treatment with FK-565 and IL-2 at Different Times Before Infection

| Dose FK-565 μg | IL-2 units | Treatment Begun on Day −7 | Treatment Begun on Day −3 |
|---|---|---|---|
| 0   | 0    | 0         | 0 |
| 4   | 0    | 6.7       | 6.7 |
| 4   | 10   | 27.0 (2)  | 0 |
| 4   | 100  | 20.0 (1)  | 20.0 (1) |
| 4   | 1000 | 40.0 (4)  | 0 |
| 20  | 0    | 6.7       | 13.3 |
| 20  | 10   | 20.0 (1)  | 13.3 |
| 20  | 100  | 13.3      | 26.7 (2) |
| 20  | 1000 | 33.0 (3)  | 40.0 (4) |
| 100 | 0    | 6.7       | 26.7 (2) |
| 100 | 10   | 6.7       | 20.0 |
| 100 | 100  | 13.0      | 33.0 (3) |
| 100 | 1000 | 6.7       | 73.0 (5) |
| 500 | 0    | 26.7 (3)  | 33.3 (3) |
| 500 | 10   | 47.0 (5)  | 20.0 (1) |
| 500 | 100  | 40.4 (4)  | 60.0 (5) |
| 500 | 1000 | 33.0 (3)  | 53.0 (5) |
| 0   | 10   | 13.3      | 13.3 |
| 0   | 100  | 20.0 (1)  | 6.7 |
| 0   | 1000 | 0.0       | 0.0 |

Numbers in parentheses represent statistical significance as determined from binomial and Poisson distribution tables:
1. $P < 0.04$
2. $P < 0.006$
3. $P < 0.0006$
4. $P < 0.001$
5. No probability of randomness.

TABLE 7

Effects of rIL-2 and FK-565
One-way Murine Mixed Lymphocyte Response

| Responders | Stimulators | rIL-2 ng/ml | FK-565 µg/ml | CPM[3] MEAN | SEM |
|---|---|---|---|---|---|
| C57BL/6[1] | C57BL/6[2] | 0.0 | — | 2046 | 377 |
| | | 10.0 | — | 33341 | 1412 |
| | | — | 0.0 | 6201 | 632 |
| | | — | 0.1 | 9503 | 535 |
| | | — | 1.0 | 9192 | 632 |
| | | — | 10.0 | 9610 | 503 |
| | | 10.0 | 0.1 | 40976 | 2409 |
| | | 10.0 | 1.0 | 38194 | 720 |
| | | 10.0 | 10.0 | 107827 | 3262 |
| C57BL/6[1] | Balb/c[2] | 0.0 | — | 72730 | 4059 |
| | | 10.0 | — | 95659 | 3476 |
| | | — | 0.0 | 79573 | 2407 |
| | | — | 0.1 | 64899 | 3189 |
| | | — | 1.0 | 66834 | 5688 |
| | | — | 10.0 | 59410 | 2567 |
| | | 10.0 | 0.1 | 123560 | 9234 |
| | | 10.0 | 1.0 | 114008 | 2670 |
| | | 10.0 | 10.0 | 118853 | 1614 |
| Balb/c[2] | Balb/c[2] | 0.0 | — | 665 | 61 |
| | | 10.0 | — | 1545 | 56 |
| | | — | 0.0 | 650 | 36 |
| | | — | 0.1 | 3634 | 2333 |
| | | — | 1.0 | 667 | 57 |
| | | — | 10.0 | 650 | 24 |

[1]Single cell suspensions were prepared from the spleens of normal mice of the specified haplotypes.
[2]Stimulator populations were treated with mitomycin-C prior to culture initiation to prevent tritiated thymidine uptake by these cells.
[3]CPM were calculated from triplicate cultures. SEM = standard error of the mean

TABLE 8

Primary In Vitro Immunization of Murine Spleen Cells
Effects of rIL-2 and FK-565

| rIL-2 ng/ml | FK-565 µg/ml | ShE | day 3 PFC/ml | % POS | day 4 PFC/ml | % POS | day 5 PFC/ml | % POS |
|---|---|---|---|---|---|---|---|---|
| — | — | — — — | 10 | 8 | 100 | 3 | 75 | 2 |
| — | — | +++ | 130 | 104 | 3290 | 108 | 3575 | 101 |
| — | 0.1 | +++ | 60 | 48 | 2260 | 74 | 4725 | 134 |
| — | 1 | +++ | 90 | 72 | 2060 | 67 | 3700 | 105 |
| — | 10 | +++ | 70 | 56 | 1430 | 47 | 2975 | 84 |
| 0.1 | — | +++ | 160 | 128 | 3990 | 130 | 1975 | 56 |
| 1 | — | +++ | 930 | 744 | 7720 | 252 | 5125 | 145 |
| 10 | — | +++ | 1840 | 1472 | 9380 | 307 | 7200 | 204 |
| 1 | 0.1 | +++ | 860 | 688 | 10020 | 327 | 6900 | 196 |
| 10 | 0.1 | +++ | 1250 | 1000 | 8360 | 273 | 10050 | 285 |
| 1 | 1 | +++ | 530 | 424 | 2890 | 94 | 3025 | 86 |
| 10 | 1 | +++ | 1360 | 1088 | 7040 | 230 | 10925 | 310 |
| 1 | 10 | +++ | 460 | 368 | 2270 | 74 | 3700 | 105 |
| 10 | 10 | +++ | 940 | 752 | 6910 | 226 | 11550 | 328 |
| — | — | +++ | 120 | 96 | 2830 | 92 | 3475 | 99 |
| — | — | — — — | 10 | 8 | 10 | 0 | 25 | 1 | ng signifies nanograms
Results are expressed as plaque-forming-cells PFC per one ml culture. PFCs were determined after 3, 4 and 5 days of culture using the slide modification of the Jerne plaque-forming-cell assay. Results from experimental groups are also expressed as a percentage of the positive control groups.

TABLE 9

Mean Cunts Per Minute for Each Triplicate Concentrations
OVA-FITC

| µg/ml | | | | IL-2 | FK-56 |
|---|---|---|---|---|---|
| 0 | 2.5 | 5.0 | 10.0 | µg/ml | µg/ml |
| 2553 ± 135 | 18958 ± 553 | 22109 ± 192 | 25067 ± 1673 | 0 | 0 |
| 4116 ± 53 | 14849 ± 478 | 20507 ± 2332 | 26114 ± 1280 | 0 | 0.01 |
| 9986 ± 491 | 27209 ± 2084 | 24563 ± 965 | 36382 ± 572 | 0 | 0.1 |
| 15458 ± 788 | 40728 ± 2191 | 48726 ± 1660 | 69954 ± 2933 | 0.3 | 0 |
| 33707 ± 935 | 65110 ± 4091 | 67694 ± 6504 | 96469 ± 622 | 0.3 | 0.01 |
| 35935 ± 2277 | 67072 ± 1471 | 76539 ± 3239 | 110443 ± 3730 | 0.3 | 0.1 |
| 16645 ± 127 | 44010 ± 170 | 51233 ± 1926 | 45687 ± 3211 | 0.6 | 0 |
| 48453 ± 2357 | 108325 ± 3600 | 112349 ± 5264 | 113128 ± 8437 | 0.6 | 0.01 |
| 61693 ± 1273 | 103677 ± 4439 | 114936 ± 5330 | 110131 ± 60267 | 0.6 | 0.1 |

TABLE 10

Mean Counts Per Minute for Each Triplicate

| FK-565 µg/ml | FK-565 Counts | IL-2 + FK-565 15 ng/ml | IL-2 + FK-565 30 ng/ml |
|---|---|---|---|
| 0 | 747 | 22326 ± 4118 | 97502 ± 1331 |
| 0.0312 | 523 | 27763 ± 1585 | 87139 ± 2640 |
| 0.125 | 883 | 36295 ± 481 | 94565 ± 1653 |
| 0.25 | 641 | 40077 ± 2710 | 90035 ± 3116 |
| 0.5 | 480 | 38039 ± 2759 | 98202 ± 423 |
| 1.0 | 874 | 79607 ± 3368 | 98896 ± 2614 |

TABLE 10-continued

| Mean Counts Per Minute for Each Triplicate | | | |
|---|---|---|---|
| FK-565 µg/ml | FK-565 Counts | IL-2 + FK-565 15 ng/ml | IL-2 + FK-565 30 ng/ml |
| 2.0 | 784 | 92147 ± 1566 | 106381 ± 1458 | ng signifies nanograms

What is claimed is:

1. A method for synergistically stimulating an animal's immune system to increase resistance to infection and disease and decrease the recovery time from injury or other trauma, which comprises:
   administering in conjunction to said animal an immune stimulating amount of FK-565 and IL-2.

2. The method of claim 1 wherein FK-565 is administered to said animal in an amount from about 0.001–1000 µg/kg body weight and IL-2 is administered to said animal in an amount from about $10^1$–$10^8$ units.

3. The method of claim 1 wherein FK-565 is administered orally and IL-2 is administered parenterally.

4. The method of claim 3 wherein said oral administration method is selected from the group consisting of administering said compound to said animals in tablets, suspensions, solutions, emulsions, capsules, powders, syrups, drinking water compositions, and feed compositions.

5. The method of claim 4 wherein FK-565 is administered in a feed composition, said feed composition further comprising:
   a nutritionally balanced feed; and
   an immune stimulating amount of FK-565 admixed with said feed.

6. The method of claim 1 wherein FK-565 is administered nasally and IL-2 is administered parenterally.

7. The method of claim 1 wherein FK-565 and IL-2 are administered parenterally.

8. The method of claim 7 wherein FK-565 and IL-2 are administered in a composition, said composition comprising:
   IL-2,
   FK-565, and
   a pharmaceutically acceptable carrier.

9. The method of claim 7 wherein FK-565 and IL-2 are administered using an implant, said implant further comprising:
   a biocompatible and FK-565 and IL-2 compatible implant material; and
   an immune stimulating amount of FK-565 and IL-2.

10. The method of claim 9 wherein FK-565 is administered to said animal in an amount from about 0.001–1000 µg/kg body weight/day and IL-2 is administered to said animal in an amount from about $10^1$–$10^8$ units/day.

11. The method of claim 7 wherein FK-565 and IL-2 are administered in an injectable formulation, said injectable formulation comprising:
   a biocompatible and FK-565 and IL-2 compatible vehicle; and
   an immune stimulating amount of FK-565 and IL-2 admixed with said vehicle.

12. The method of claim 1 wherein said animal is selected from the group consisting of human, bovine, porcine, canine, feline, equine, avian, and ovine species.

13. The method of claim 12 wherein said animal is selected from the group consisting of cattle, swine, sheep, chickens, and turkeys.

14. An immunostimulating composition suitable for synergistically stimulating an animal's immune system to increase resistance to infection and disease and decrease the recovery time from injury or other trauma or functioning as an adjuvant, which comprises:
   IL-2,
   FK-565, and
   a pharmaceutically acceptable carrier.

15. The composition of claim 14 wherein the amount of FK-565 in said composition is from about 0.001–1000 µg/kg body weight and the amount of IL-2 in said composition is from about $10^1$–$10^8$ units.

16. A method for enhancing the efficacy of a vaccine administered to an animal, comprising:
   administering in conjunction an adjuvant comprising FK-565 and IL-2; and
   a vaccine.

17. The method of claim 16 wherein said FK-565 is administered in dosages of from about 0.001–1000 µg/kg body weight and IL-2 is administered in dosages of from about $10^1$–$10^8$ units.

18. The method of claim 16 wherein said adjuvant is administered independently of said vaccine prior to, contemporaneously with, or subsequent to said vaccine administration.

19. The method of claim 16 wherein said adjuvant is incorporated in said vaccine.

20. The method of claim 17 wherein said adjuvant is incorporated in said vaccine in an amount from about 0.001–1000 µg/kg body weight and IL-2 is administered to said animal in an amount from about $10^1$–$10^8$ units.

21. An article of manufacture for synergistically stimulating an animal's immune system with FK-565 and IL-2 to increase resistance to infection and disease and decrease the recovery time from injury or other trauma, which comprises:
   a first container containing an immunostimulating amount of FK-565 in a pharmaceutically acceptable carrier suitable for parenteral or oral administration; and
   a second container containing an immunostimulating amount of IL-2 in a pharmaceutically acceptable carrier suitable for parenteral administration.

22. The article of manufacture of claim 21 wherein the first container contains from about 0.001–1000 µg FK-565/kg body weight.

23. The article of manufacture of claim 21 wherein the second container contains from about $10^1$–$10^8$ units IL-2.

24. An article of manufacture for synergistically stimulating an animal's immune system with FK-565 and IL-2 to increase resistance to infect and disease and decrease the recovery time from injury or other trauma, which comprises:
   a container containing an immunostimulating amount of:
   IL-2,
   FK-565, and
   a pharmaceutically acceptable carrier.

25. The article of manufacture of claim 24 wherein the container contains from about 0.001–1000 µg FK-565/kg body weight and from about $10^1$–$10^8$ unit IL-2.

* * * * *

UNITED STATES PATENT AND TRADEMARK OFFICE
CERTIFICATE OF CORRECTION

PATENT NO. : 4,938,956

DATED : July 3, 1990

INVENTOR(S) : D. K. Howard et al

It is certified that error appears in the above-identified patent and that said Letters Patent is hereby corrected as shown below:

Column 1, line 62, "activiries" should read --activities--.

Column 16, Table 9, in the Heading, "Cunts" should read --Counts--.

Column 16, Table 9, In the Heading, "FK-56" should read --FK-565--.

Signed and Sealed this

Twenty-third Day of March, 1993

Attest:

STEPHEN G. KUNIN

Attesting Officer

Acting Commissioner of Patents and Trademarks